United States Patent [19]
Backer et al.

[11] Patent Number: 5,843,925
[45] Date of Patent: Dec. 1, 1998

[54] METHODS FOR INHIBITING ANGIOGENESIS, PROLIFERATION OF ENDOTHELIAL OR TUMOR CELLS AND TUMOR GROWTH

[75] Inventors: Joseph M. Backer, Tenafly, N.J.; Peter Bohlen, Cortland Manor, N.Y.

[73] Assignee: American Cyanamid Company, Madison, N.J.

[21] Appl. No.: 354,694

[22] Filed: Dec. 13, 1994

[51] Int. Cl.$^6$ .............................. A61K 31/65; A61K 9/26
[52] U.S. Cl. ......................... 514/152; 514/154; 514/765; 514/768; 424/469; 424/470
[58] Field of Search .................... 514/154, 152, 514/765, 768; 424/469, 470

[56] References Cited

U.S. PATENT DOCUMENTS

| | | | |
|---|---|---|---|
| 3,226,436 | 12/1965 | Petisi et al. | 260/559 |
| 3,518,306 | 6/1970 | Martell et al. | 260/559 |
| 5,248,797 | 9/1993 | Sum | 552/205 |
| 5,268,384 | 12/1993 | Galardy | 514/419 |
| 5,328,902 | 7/1994 | Sum et al. | 514/152 |
| 5,563,130 | 10/1996 | Backer et al. | 514/152 |
| 5,567,693 | 10/1996 | Backer et al. | 514/154 |
| 5,574,026 | 11/1996 | Backer et al. | 514/152 |

FOREIGN PATENT DOCUMENTS

92/12717  8/1992  WIPO.

OTHER PUBLICATIONS

Guerin. C. et al, Selective Endothelial Growth Inhibition by Tetracyclines that Inhibit Collagenase, *Biochemical and Biophysical Research Communications*, vol. 188, No. 2, 740–745, 1992.

Bogert, C. van den et al, Arrest of in Vivo Proliferation of Zajdela Tumor Cells by Inhibition of mitochondrial protein Synthesis, *Cancer Research* 41, 194–1947, May 1981.

Teicher, B. A. et al, Antiangiogenic Agents Potentiate Cytotoxic Cancer Therapies against Primary and Metastatic Disease, *Cancer Research* 52, 6702–6704, Dec. 1992.

Monks, A. et al, Feasibility of a High–Flux Anticancer Drug Screen Using a Diverse Panel of Cultured Human Tumor Cell Lines, *Journal of the National Cancer Institute*, vol. 83, No. 11, 757–766, Jun. 1991.

Sotomayor, E. A. et al, Minocycline in combination with chemotherapy or radiation therapy in vitro and in vivo, *Cancer Chemotherapy and Pharmacology*, 30:377–384, 1992.

Leezenberg, J.A. et al, Possible Cytostatic Action of Tetracyclines in the Treatment of Tumors of the Nasopharynx and Larynx, *European Journal of Clinical Pharmacology*, 16, 237–241, 1971.

Tamargo, R. et al, Angiogenesis Inhibition by Minocycline, *Cancer Research* 51, 672–675, Jan. 1991.

Kroon A.M. et al, The Antitumour Action of Doxycycline, *Drugs Exptl. Clin. Res.*, X(11), 759–766, 1984.

Bogert C. van den, Arrest of the Proliferation of Renal and Prostate Carcinomas of Human Origin by Inhibition of Mitochondrial Protein Synthesis, *Cancer Research*, 46, 3283–3289, Jul. 1986.

Pruzanski, W. et al, Inhibition of Enzymatic Activity of Phospholiphases $A_2$ by Minocycline and Doxycycline, *Biochemical Pharmacology*, vol. 44, No. 6, 1165–1170, 1992.

Golub, L.M. et al, Host Modulation with Tetracyclines and their Chemically Modified Analogues, *Periodontology and Restorative Dentistry*, 80–90, 1992.

Golub, L. M. et al Tetracyclines Inhibit Connective Tissue Breakdown: New Therapeutic Implications for an Old Family of Drugs, *Critical Reviews in Oral Biology and Medicine*, 2(2):297–322 (1991).

Zucker, S. et al, Diversity of Melanoma Plasma Membrane Proteinases: Inhibition of Collagenoloytic and Cytolytic Activities by Minocycline, *JNCI*. vol. 75, No. 3, Sep. 1985.

Greenwald R. A., et al, Tetracyclines Inhibit Human Synovial Collagenase in Vivo and In Vitro, *The Journal of Rheumatology* 1987: 14:1.

Hlavka, J. et al, The 6–Deoxytetracyclines.III.Electrophilic and Nucleophilic Substitution *J. AM. Chem. Soc.*, 84, 1420, 1962.

*Primary Examiner*—Chhaya D. Sayala
*Attorney, Agent, or Firm*—Michael R. Nagy

[57] ABSTRACT

The invention relates to a method for inhibiting angiogenesis and proliferation of endothelial cells by administering an inhibitory amount of a 7-[substituted amino]-9-[(substituted glycyl)amido]-6-demethyl-6-deoxytetracycline of Formula I:

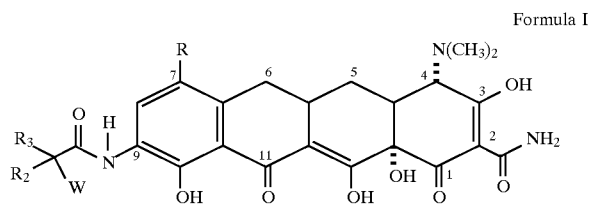

Formula I wherein R, $R_2$, $R_3$, and W are as defined in the specification. The invention also relates to a method for inhibiting proliferation of tumor cells and tumor growth by administering an inhibitory amount of a compound of Formula I in combination with a chemotherapeutic agent or radiation therapy. The invention also relates to compositions containing an effective inhibitory amount of a compound of Formula I in a pharmaceutically acceptable carrier.

16 Claims, 2 Drawing Sheets

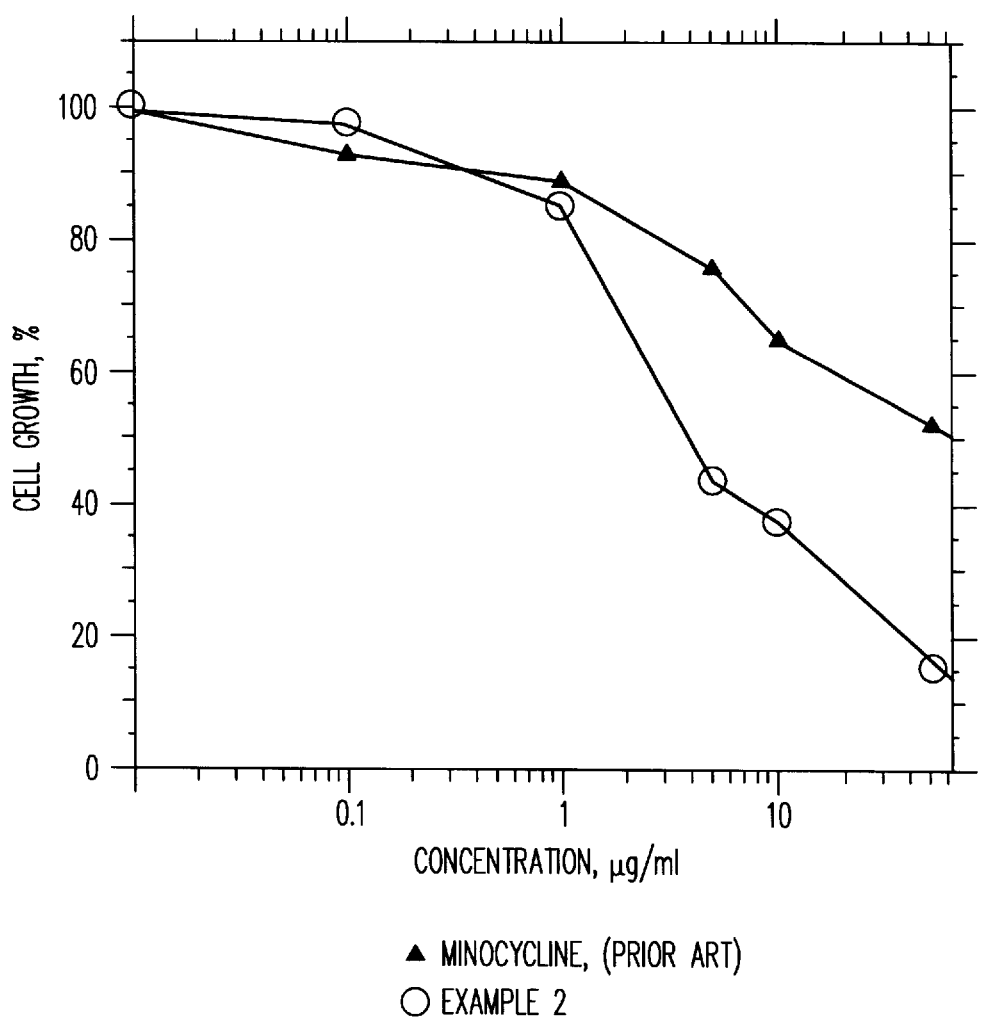

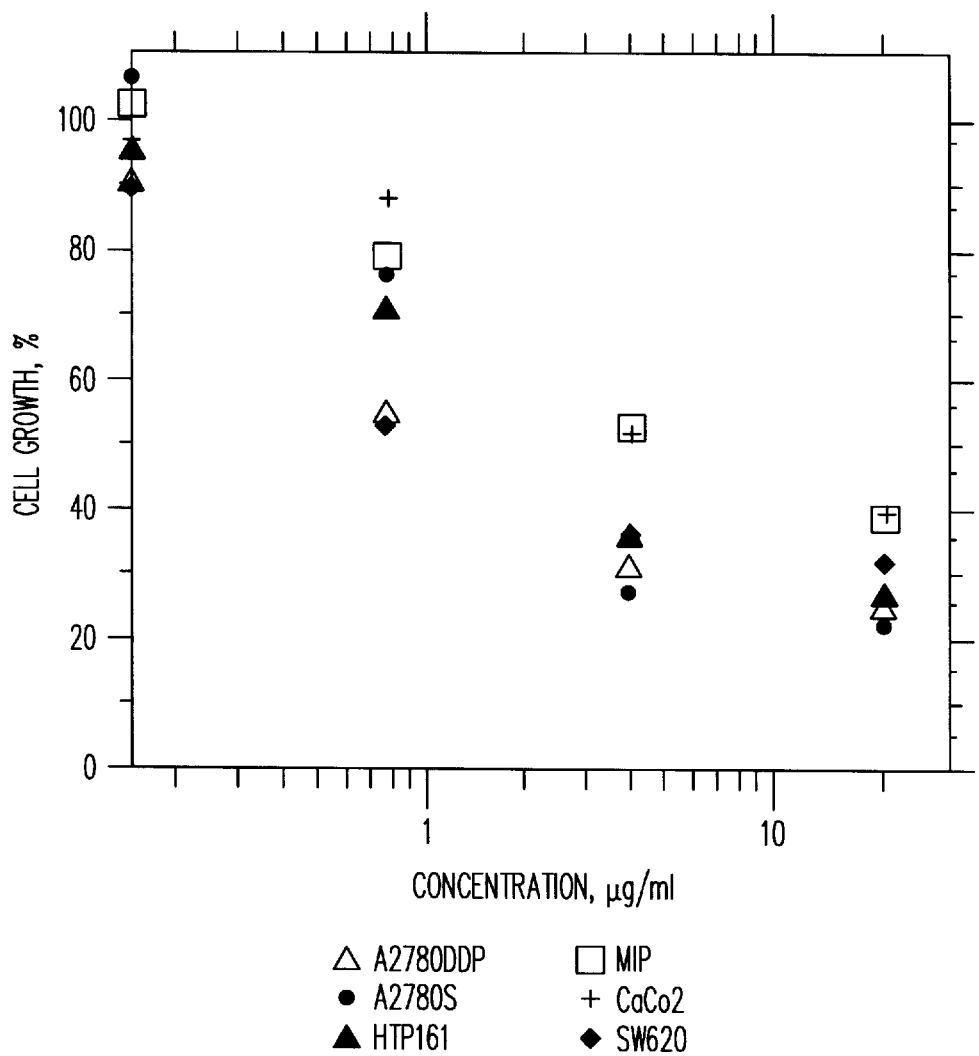

METHODS FOR INHIBITING ANGIOGENESIS, PROLIFERATION OF ENDOTHELIAL OR TUMOR CELLS AND TUMOR GROWTH

BACKGROUND OF THE INVENTION

1. Field of the Invention

The invention relates to a method for inhibiting angiogenesis and proliferation of endothelial cells by administering an inhibitory amount of a 7-[substituted amino]-9-[(substituted glycyl)amido]-6-demethyl-6-deoxytetracycline. The invention also relates to a method for inhibiting proliferation of tumor cells and tumor growth by administering an inhibitory amount of a 7-[substituted amino]-9-[(substituted glycyl)amido]-6-demethyl-6-deoxytetracycline in combination with a chemotherapeutic agent or radiation therapy. The invention also relates to compositions containing an effective inhibitory amount of a 7-[substituted amino]-9-[(substituted glycyl)amido]-6-demethyl-6-deoxytetracycline in a pharmaceutically acceptable carrier.

2. Description of the Prior Art

In WO92/12717, Brem et al teach that some tetracyclines, particularly Minocycline, Chlortetracycline, Demeclocycline and Lymecycline are useful as inhibitors of angiogenesis. In *Cancer Research* 51, 672–675, Jan. 15, 1991, Brem et al teach that Minocycline inhibits angiogenesis to an extent comparable to that of the combination therapy of heparin and cortisone. In *Cancer Research* 52, 6702–6704, Dec. 1, 1992, Teicher et al teach that tumor growth is decreased and the number of metastases is reduced when the anti-angiogenic agent of metastases is reduced when the anti-angiogenic agent Minocycline is used in conjunction with cancer chemotherapy or radiation therapy.

It has now been found that certain 7-[substituted amino]-9-[(substituted glycyl)amido]-6-demethyl-6-deoxytetracyclines are unexpectedly better inhibitors of endothelial and tumor cell proliferation than the tetracyclines, especially Minocycline, described by Brem et al and Teicher et al.

SUMMARY OF THE INVENTION

The invention provides a method for inhibiting angiogenesis and endothelial cell proliferation which comprises administering an effective inhibitory amount of a compound of formula I:

Formula I wherein

R is a (disubstituted) amino of the formula —N(R$_4$)(R$_5$) and (R$_4$) and (R$_5$) may be the same or different and are selected from straight or branched (C$_1$–C$_4$)alkyl, or [(C$_3$–C$_6$)cycloalkyl](C$_1$–C$_4$)alkyl;

W is (R$_1$)$_2$—N—; R$_1$—NH— or (C$_2$–C$_5$)azacycloalkane wherein

R$_1$ is a straight chain (C$_1$–C$_7$)alkyl;

R$_2$ is hydrogen or (C$_1$–C$_3$)alkyl;

R$_3$ is hydrogen or (C$_1$–C$_3$)alkyl; or a pharmaceutically acceptable salt thereof;

alone or in combination with a therapeutic agent used in the treatment of an angiogenic disorder; to a warm blooded animal having a disorder characterized by the undesired proliferation of endothelial cells.

The invention also provides a method for inhibiting tumor cell proliferation and tumor growth which comprises administering an effective inhibitory amount of a compound of formula I:

Formula I wherein

R is a (disubstituted) amino of the formula —N(R$_4$)(R$_5$) and (R$_4$) and (R$_5$) may be the same or different and are selected from straight or branched (C$_1$–C$_4$)alkyl, or [(C$_3$–C$_6$)cycloalkyl](C$_1$–C$_4$)alkyl;

W is (R$_1$)$_2$—N—; R$_1$—NH— or (C$_2$–C$_5$)azacycloalkane wherein

R$_1$ is a straight chain (C$_1$–C$_7$)alkyl;

R$_2$ is hydrogen or (C$_1$–C$_3$)alkyl;

R$_3$ is hydrogen or (C$_1$–C$_3$)alkyl; or a pharmaceutically acceptable salt thereof;

in combination with a chemotherapeutic agent or radiation therapy; to a warm blooded animal having a disorder characterized by the undesired proliferation of tumor cells.

The invention also provides a composition for inhibiting angiogenesis and endothelial cell proliferation which composition comprises an amount effective for inhibiting endothelial cell proliferation of a compound of formula I:

Formula I wherein

R is a disubstituted amino of the formula —N(R$_4$)(R$_5$) and (R$_4$) and (R$_5$) may be the same or different and are selected from straight or branched (C$_1$–C$_4$)alkyl, or [(C$_3$–C$_6$)cycloalkyl)(C$_1$–C$_4$)alkyl;

W is (R$_1$)$_2$—N—; R$_1$—NH— or (C$_2$–C$_5$)azacycloalkane wherein

R$_1$ is a straight chain (C$_1$–C$_7$)alkyl;

R$_2$ is hydrogen or (C$_1$–C$_3$)alkyl;

R$_3$ is hydrogen or (C$_1$–C$_3$)alkyl; or a pharmaceutically acceptable salt thereof;

in a pharmaceutical carrier for administration to a warm blooded animal having a disorder characterized by undesired proliferation of endothelial cells.

The invention also provides a composition for inhibiting tumor cell proliferation and tumor growth which composition comprises an amount effective for inhibiting tumor cell proliferation of a compound of formula I:

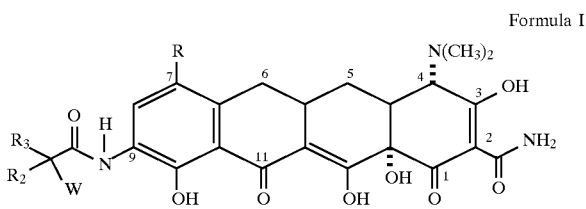

Formula I wherein

R is a disubstituted amino of the formula —N(R$_4$)(R$_5$) and (R$_4$) and (R$_5$) may be the same or different and are selected from straight or branched (C$_1$–C$_4$)alkyl, or [(C$_3$–C$_6$)cycloalkyl](C$_1$–C$_4$)alkyl;

W is (R$_1$)$_2$—N—; R$_1$—NH— or (C$_2$–C$_5$)azacycloalkane wherein

R$_1$ is a straight chain (C$_1$–C$_7$)alkyl;

R$_2$ is hydrogen or (C$_1$–C$_3$)alkyl;

R$_3$ is hydrogen or (C$_1$–C$_3$)alkyl; or a pharmaceutically acceptable salt thereof;

in a pharmaceutical carrier for administration to a warm blooded animal having a disorder characterized by the undesired proliferation of tumor cells.

DESCRIPTION OF THE DRAWINGS

FIG. 1 depicts the effects of the compound of Example 2 on the proliferation of Adult Bovine Aortic Endothelial cells (ABAE) compared to the prior art compound, Minocycline.

FIG. 2 depicts the effects of the compound of Example 8 on the cell growth of 6 Human Tumor cell lines.

DESCRIPTION OF THE PREFERRED EMBODIMENT

Angiogenesis, a biological process that includes the proliferation and migration of endothelial cells, is defined as the growth of new blood vessels, in particular, capillaries and is an essential part of both normal and pathological tissue growth. Characteristic elements of angiogenesis include endothelial cell proliferation, endothelial cell migration, invasion of endothelial cells into tissue, tube formation, and maturation of endothelial cells. Angiogenesis plays a critical role in such beneficial functions as embryogenesis, wound healing and the female reproductive cycle, as well as in such abnormal functions as psoriasis, diabetic retinopathy, rheumatoid arthritis, hemangiomas, and solid tumor formation.

It has now been found that administration of an effective amount of a compound of Formula I inhibits endothelial cell proliferation and tube formation, having the effect of preventing new capillary blood vessels from forming and thus inhibiting angiogenesis. In particular, the compounds of Formula I are cytostatic for endothelial cells, i.e., they inhibit the ability of the cells to divide without affecting other vital cell functions. According to the present invention, angiogenesis is inhibited by the administration of an effective amount of a compound of Formula I. In this regard, the effective amount of a compound of Formula I for inhibiting angiogenesis and endothelial cell proliferation is from about 0.10 mg/kg to about 30.0 mg/kg of body weight, with from about 1.0 mg/kg to about 10.0 mg/kg of body weight being preferred.

The ingrowth of capillaries and ancillary blood vessels is essential for growth of solid tumors and is thus an unwanted physiological response which facilitates the spread of malignant tissue and metastases. Inhibition of angiogenesis and the resultant growth of capillaries and blood vessels is therefore a component of effective treatment of malignancy.

The compounds of Formula I may be administered alone or in combination with another therapeutic agent used in the treatment of an angiogenic disorder. Such therapeutic agents include, for example, methotrexate, angiostatin, genistein, suramin, pentosan polysulfate, thalidomide and 2-methoxyestradiol.

The fact that administration of a compound of Formula I inhibits angiogenesis and endothelial cell proliferation to a remarkable degree is quite beneficial for controlling the growth of solid tumors because most if not all solid tumors, like normal tissue, require a steady and sufficient blood supply for optimal growth. Tumors are known to make use of angiogenic growth factors that are produced by the tumor cells in order to attract new blood vessels and ascertain supply with sufficient amounts of nutrients to sustain their growth. Many tumors are well vascularized and the inhibition of the formation of an adequate blood supply to the tumor by inhibition of tumor vascularization, as a result of endothelial cell growth inhibition, is beneficial in tumor growth control. Without a strong blood supply, rapid and prolonged growth of tumor tissue cannot be sustained.

It has also been found that the compounds of Formula I are cytostatic for tumor cell proliferation. The fact that both tumor and endothelial cells are growth inhibited by administration of a compound of Formula I is desirable and advantageous. From a mechanistic point of view, the effect of a compound of Formula I on tumor growth is a dual one, by acting on tumor cell inhibition directly and by reduction of the blood supply indirectly. Both aspects contribute to inhibition of tumor growth and a compound that combines these aspects is extremely advantageous over other drugs which act on only one of the targets.

The administration of a compound of Formula I is effective in controlling the growth of solid tumors. Examples of solid tumors include but are not limited to colon tumors, ovarian tumors, breast tumors, lung tumors, pancreatic, osteosarcoma, prostate and melanoma tumors.

According to the present invention, tumor growth is inhibited by administering an effective amount of a compound of Formula I to a patient having a disorder characterized by the undesired proliferation of solid tumor cells. In this regard, the effective dosage of compound of Formula I for inhibiting tumor cell proliferation and tumor growth is from about 0.10 mg/kg to about 30.0 mg/kg of body weight, with from about 1.0 mg/kg to about 10.0 mg/kg of body weight being preferred.

The compounds of Formula I may be administered alone or in conjunction with a standard tumor therapy, such as chemotherapy or radiation therapy. It is preferred that the compounds of Formula I be administered in combination with a standard therapy: chemotherapy or radiation therapy. While not wishing to be bound by any theory, it appears that the clear effect of the administration of a compound of Formula I to inhibit tumor growth is related to the ability of the compound to inhibit endothelial cell proliferation and hence new blood vessel formation. Such reduction of vascular supply works best when a tumor is significantly reduced in mass after standard chemotherapy or radiation therapy. It is significant that the compound of Formula I can be administered in conjunction with the standard antitumor therapy and, in addition, can be administered on a continuing basis after the standard antitumor therapy. In this way the tumor will grow back slower while the patient is recovering from the side effects of the standard therapy. Chemotherapy or radiation therapy can then be repeated along with the continuation of the administration of compound of Formula I. The effect of this continuation of combination therapy is that the compound of Formula I will be effective in slowing down vascular supply to an already weakened tumor until it is essentially eradicated.

It is also contemplated that administration of a compound of Formula I controls metastases. Metastases also require a blood supply in order to become full blown secondary tumors. Since, some metastases are small, administration of a compound of Formula I directly counteracts the angiogenic signal of metastases. Such a compound also contributes to slower metastasis growth because it has a direct effect on tumor cell proliferation.

The compound of Formula I may be administered orally, parentarelly, topically, intravenously, or systemically. In addition, for inhibiting tumor cell proliferation and tumor growth, the compound of Formula I may be administered locally directly to the tumor or as a part of a deposited slow release formulation. Administration may be on a daily basis for as long as needed to inhibit angiogenesis, endothelial cell proliferation, tumor cell proliferation or tumor growth. Alternatively, a slow release formulation may continue for as long as needed to control tumor growth. This dosage regimen may be adjusted to provide the optimum therapeutic response. For example, several divided doses may be administered daily or the dose may be proportionally reduced as indicated by the exigencies of the therapeutic situation.

In this regard, the compositions of this invention that are useful as inhibitors of angiogenesis, endothelial cell proliferation, tumor cell proliferation and tumor growth contain a pharmaceutically acceptable carrier and an amount of a compound of Formula I, 7-[substituted amino)-9-[(substituted glycyl)amido]-6-demethyl-6-deoxytetracycline or a pharmaceutically acceptable salt thereof, effective to inhibit tumor or endothelial cell proliferation.

The pharmaceutically acceptable salts of the 7-[substituted amino]-9-[(substituted glycyl)amido]-6-demethyl-6-deoxytetracyclines include inorganic salts such as hydrochloride, hydrobromide, hydroiodide, phosphate, nitrate or sulfate; or organic salts such as acetate, benzoate, citrate, cysteine or other amino acids, fumarate, glycolate, maleate, succinate, tartrate, alkylsulfonate or arylsulfonate. It is contemplated that the 7-[substituted amino]-9-[(substituted glycyl)amido]-6-demethyl-6-deoxytetracyclines may also be utilized as metal complexes, for 5 example, aluminum, calcium and iron; or as the corresponding Mannich base adducts using methods known to those skilled in the art (Richard C. Larock, Comprehensive Organic Transformations, VCH Publishers, 411–415, 1989). It is known to one skilled in the art that an appropriate salt form is chosen based on physical and chemical stability, flowability, hygroscopicity and solubility. It is also known to those skilled in the art, that the above salts are made from the corresponding acid, so that hydrochloric acid gives the hydrochloride salt, sulfuric acid gives the sulfate salt, and acetic acid gives the acetate salt.

Depending on the stoichiometry of the above acids used, the salt formation occurs at the C(4)-ring position which has a dimethylamino group (1 equivalent of acid); or with both the C(4)-ring position which has a dimethylamino group and the W group (2 equivalents of acid). The salts are preferred for oral and parenteral administration.

Pharmaceutical compositions are prepared using the compounds of formula I as the active agent for inhibition of tumor and/or endothelial cell proliferation based on the specific application. Any of the compositions may also include preservatives, antioxidants, inmunosuppressants, and other biologically and pharmaceutically effective agents which do not exert a detrimental effect on the 7-[substituted amino]-9-[(substituted glycyl)amido]-6-demethy1-6-deoxytetracycline or the cells. For treatment of tumor cells, the composition may include a chemotherapeutic agent for example an anti-cancer agent, many of which are known and clinically in use, which selectively kills the faster replicating tumor cells. Exemplary anti-cancer agents include melphalan, cyclophosphamide, methotrexate, adriamycin and bleomycin [Sotomayor et al, *Cancer Chemother. Pharmacol.*, (1992), 30:377–384]. It is also contemplated that the compounds of Formula I can be used to treat other angiogenic diseases, in conjunction with appropriate established therapeutic agents for example the anti-cancer agents listed above or anti-inflammatory agents, steroidal or nonsteroidal, such as the corticosteroids or endomethacins. For example, compounds of Formula I maybe used in combination with methotrexate or an anti-inflammatory agent to treat rheumatoid arthritis.

For topical application, the 7-[substituted amino]-9-[(substituted glycyl)amido]-6-demethyl-6-deoxytetracycline is combined with a carrier so that an effective dosage is delivered, based on the desired activity, at the site of application. The topical composition can be applied to the skin for treatment of diseases such as psoriasis. The carrier may be in the form of ointment, cream, gel paste, foam, aerosol, suppository, pad or gelled stick. A topical composition for treatment of eye disorders, such as diabetic retinopathy, consists of an effective amount of a compound of formula I in an ophthalmically acceptable excipient such as buffered saline, mineral oil, vegetable oils such as corn or arachis oil, petroleum jelly, Miglyl 182, alcohol solution or liposome or liposome-like product.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such benzyl alcohol or methyl parabens; antioxidants such as ascorbic acid or sodium bisulfate; chelating agents such as ethylene-diaminetetraacetic acid; buffers such as acetates, citrates, or phosphates and agents for the adjustment of tonicity such as sodium chloride or dextrose. The parental preparation can be enclosed in ampoules, disposable syringes or multiple dose vials made of glass or plastic.

Compositions for oral or systemic administration will generally include an inert diluent in addition to the compound of Formula I. Such compositions may be in the form of tablets or capsules, which can contain any of the following ingredients, or compounds of a similar nature: a binder such as microcrystalline cellulose, gum tragacanth or gelatin; an excipient such as a starch or lactose, a disintegrating agent such as alginic acid, Primogel or corn starch; a lubricant such as magnesium stearate; or a glidant such as colloidal silicon dioxide. In addition the tablets or capsules may contain various other materials which modify its physical form, for example, coatings of sugar, shellac, or other enteric agents. When a capsule is employed, it can contain in addition to material of the above type, a liquid carrier such as a fatty oil.

The compounds of formula I may also be embedded in a biocompatable controlled release matrix delivery device and inserted at the tumor site to maintain therapeutically effective levels of the compound in the target tumor. The device may be in the form of a rod, pellet, disc, microspheres, tablet or other shape and may be prepared by any of a number of methods including molding, compression, coacervation or extrusion. The device is designed to produce predictable and reproducible drug release rates. This may be a continuous zero-order profile or the formulation can be varied to give a programmed release profile which may have an initial burst, pulsatile release or another pattern which may conform to chronobiological or other therapeutic requirements. The matrix preferably contains a biodegradable polymer which may include polylactides, polyglycolide, polyanhydride, and copolymers of these substances. Nonbiodegradable polymers may also be used such as silicones or certain acrylic resins.

The compounds according to Formula I which are used for the novel methods and compositions of this invention may be readily prepared in accordance with the following scheme.

A method for producing a 7-[substituted amino]-9-[(substituted glycyl)amido]-6-demethyl-6-deoxytetracycline or its mineral acid salt, 3, is shown in Scheme I. This method uses common intermediates which are easily prepared by reacting commercially available haloacyl halides of the formula:

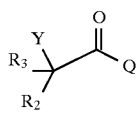

wherein $R_2$ and $R_3$ are as defined hereinabove; Q and Y are halogen selected from bromine, chlorine, iodine and fluorine;
with a 9-amino-7-[substituted amino]-6-demethyl-6-deoxytetracycline or its mineral acid salt, 1, to give 9-[(haloacyl)amido]-7-[substituted amino]-6-demethyl-6-deoxytetracycline or its mineral acid salt, 2, in almost quantitative yield. The above intermediate, 9-[(haloacyl) amido]-7-[substituted amino]-6-demethyl-6-deoxytetracycline or its mineral acid salt, 2, is reacted with a wide variety of nucleophiles, especially amines, having the formula WH, wherein W is as defined hereinabove, to give a 7-[substituted amino]-9-[(substituted glycyl)amido]-6-demethyl-6-deoxytetracycline or its mineral acid salt, 3, of the present invention.

Scheme I

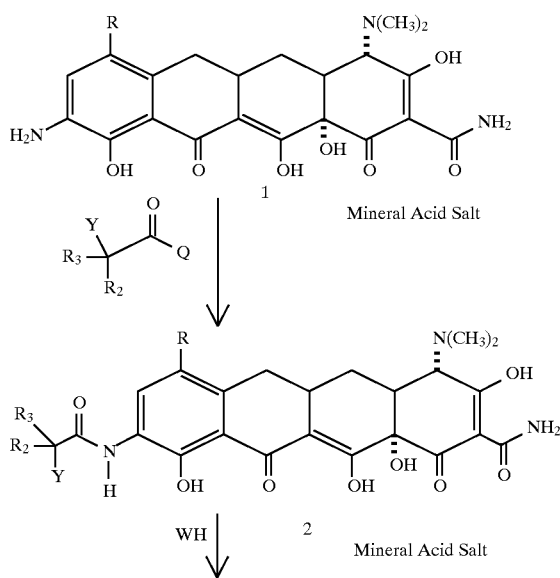

-continued
Scheme I

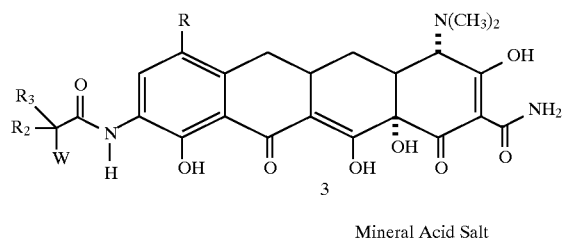

Mineral Acid Salt

In accordance with Scheme I, 9-amino-7-[substituted amino]-6-demethyl-6-deoxytetracycline or its mineral acid salt, 1, prepared by procedure known to those skilled in the art including U.S. Pat. Nos. 3,226,436; 3,518,306; 5,248,091; is mixed with:

a) a polar-aprotic solvent such as 1,3-dimethyl-3,4,5,6-tetrahydro-2(1H)pyrimidone, hereinafter called DMPU, hexamethylphosphoramide hereinafter called HMPA, dimethylformamide, dimethylacetamide, N-methylpyrrolidone, 1,2-dimethoxyethane or equivalent thereof;

b) an inert solvent such as acetonitrile, methylene chloride, tetrahydrofuran, chloroform, carbon tetrachloride, 1,2-dichloroethane, tetrachloroethane, diethyl ether, t-butyl methyl ether, isopropyl ether of equivalent thereof;

c) a base such as sodium carbonate, sodium bicarbonate, potassium bicarbonate, triethylamine, cesium carbonate, lithium carbonate or bicarbonate equivalents; and d) a haloacyl halide of the formula:

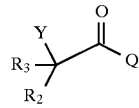

wherein Y, Q, $R_2$ and $R_3$ are as defined hereinabove, such as bromoacetyl bromide, chloroacetyl chloride, 2-bromopropionyl bromide or equivalent thereof; the halo, Y and the halide, Q, in the haloacyl halide can be the same or different halogen and are selected from bromine, chlorine, iodine and fluorine;

e) for 0.5 to 5 hours at from room temperature to the reflux temperature of the reaction; to form the corresponding 9-[(haloacyl)amido]-7-[substituted amino]-6-demethyl-6-deoxytetracycline, 2, or its mineral acid salt.

The intermediate, 9-[(haloacyl)amido]-7-[substituted amino]-6-demethyl-6-deoxytetracycline, 2, or its mineral acid salt is treated, under an inert atmosphere of helium, argon or nitrogen with a) a nucleophile, WH, such as a mono-substituted amine, disubstituted amine, or equivalent thereof for example methylamine, dimethylamine, ethylamine, n-butylamine, propylamine, n-hexylamine piperidine or pyrrolidine;

b) in a polar-aprotic solvent such as DMPU, HMPA, dimethylformamide, dimethylacetamide, n-methylpyrrolidone or 1,2-dimethyoxyethane;

c) for from 0.5 to 2 hours at room temperature or under reflux temperature to produce the desired 7-[substituted amino]-9-[(substituted glycyl)amido]-6-demethyl-6-deoxytetracyclines or the mineral acid salt, 3.

Some of the compounds according to formula I, in the hereinbefore described Scheme I, have centers of asymmetry at the carbon bearing the W substituent. The compounds may, therefore, exist in at least two (2) stereoisomeric forms.

The present invention encompasses the racemic mixture of stereoisomers as well as all stereisomers of the compounds whether free from other stereoisomers or admixed with stereoisomers in any proportion of enentiomers. The absolute configuration of any compound may be determined by conventional X-ray crystallography.

The stereochemistry centers on the tetracycline unit (i.e., C-4, C-4a, C-5a, C-12a) remain intact throughout the reaction sequence.

The following examples describe in detail the chemical synthesis of representative compounds of the present invention. The procedures are illustrations, and the invention should not be construed as being limited by chemical reactions and conditions they express. No attempt has been made to optimize the yields obtained in these reactions, and it would be obvious to one skilled in the art that variations in reaction times, temperatures, solvents, and/or reagents could increase the yields.

EXAMPLE 1

[4S-(4a 12aa-1-9-[(Chloroacetyl)amino]-4,7-bis-(dimethylamino)-1,4,4a,5,5a,6,11,12a-octahydro-3,10,12,12a-tetrahydroxy-1,11-dioxo-2-naphthacenecarboxamide dihydrochloride To a room temperature solution of 0.334 g of 9-amino-4,7-bis(dimethylamino)-6-demethyl-6-deoxy-tetracycline disulfate, 6 ml of 1,3-dimethyl-3,4,5,6-tetrahydro-2(1H)-pyrimidone (DMPU), and 2 ml of acetonitrile is added 0.318 g of sodium carbonate. The mixture is stirred for 5 minutes followed by the addition of 0.068 g of chloroacetyl chloride. The reaction is stirred for 30 minutes, filtered, and the filtrate is added dropwise to 100 ml of diethyl ether, containing 1 ml of 1M hydrochloric acid in diethyl ether. The resulting solid is collected and dried to give 0.340 g of the desired intermediate.

MS(FAB): m/z 549 (M+H).

EXAMPLE 2

[4S-(4a,12aa-1-4,7-Bis(dimethylamino)-9-[[(dimethylamino)acetyl]amino]]-1,4,,4a,5,5a,6,11,12a-octahvdro-3,10,12,12a-tetrahydroxy-1,11-dioxo-2-napththacenecarboxamide dihydrochloride To a solution of 0.15 g of product from Example 1 in 4 ml of DMPU is added 0.85 g of dimethylamine (40% in water). The reaction is stirred for 20 minutes followed by concentration in vacuo to remove the excess dimethylamine. The mixture is filtered and the filtrate added, dropwise, to 70 ml of isopropyl alcohol/diethyl ether (1:1). To this solution is added 1 ml of 1M hydrochloric acid/diethyl ether. The resulting precipitate is collected, washed with isopropyl alcohol and diethyl ether, and dried to give 0.11 g of the desired product.

MS(FAB): m/z 558 (M+H).

Substantially following the methods described in detail hereinabove in Example 2, the compounds of this invention listed below in Table 1 (Examples 3–8) are prepared.

TABLE 1

| Example No. | Name of Product | Reactant | MS(FAB):m/z |
|---|---|---|---|
| 3 | [7S-(7α,10aα)]-N-[9-(Aminocarbonyl)-4,7-bis(dimethylamino)-5,5a,6,6a,7,10,10a,12-octahydro-1,8–10a,11-tetrahydroxy-10,12-dioxo-2-naphthacenyl]-1-pyrrolidine-acetamide dihydrochloride | Pyrrolidine | 584 (M + H) |
| 4 | [4S-(4α,12aα)]-4,7-Bis(dimethylamino)-9-[(hexylamino)acetyl]amino]-1,4,4a,5,5a,6,-11,12a-octahydro-3,10,12,12a-tetrahydroxy-1,11-dioxo-2-naphthacenecarboxamide dihydrochloride | Hexylamine | 614 (M + H) |
| 5 | [4S-(4α,12aα)]-4,7-Bis(dimethylamino)-9-[[(heptylamino)acetyl]amino]-1,4,4a,5,5a,-6,11,12a-octahydro-3,10,12,12a-tetra-hydroxy-1,11-dioxo-2-naphthacene-carboxamide dihydrochloride | Heptylamine | 628 (M + H) |
| 6 | [4S-(4α,12aα)]-4-(Dimethylamino)-9-[[(dimethylamino)acetyl]amino]-7-(dipropylamino)-1,4,4a,5,5a,6,11,12a-octahydro-3,10,12,12a-tetrahydroxy-1,11-dioxo-2-naphthacenecarboxamide sulfate (1:1) | Dimethylamine | 614 (M + H) |
| 7 | 7-[Butyl(cyclopropylmethyl)amino]-4-(dimethylamino)-9 [[(dimethylamino)-acetyl]amino]-1,4,4a,5,5a,6,-11,12a-octahydro-3,10,12,12a-tetrahydroxy-1,11-dioxo-2-naphthacenecarboxamide sulfate (1:2) | Dimethylamino | 640 (M + H) |
| 8 | [4S-(4α,12aα)]-7-[Bis(2-methylpropyl)-amino]-4-(dimethylamino)9-[[(dimethyl-amino)acetyl]amino]-1,4,4a,5,5a,6,-11,12a-octahydro-3,10,12,12a-tetrahydroxy-1,11-dioxo-2-naphthacenecarboxamide sulfate | Dimethylamino | 642 (M + H) |

BIOLOGICAL ACTIVITY

The antiproliferative activity of the compounds of Formula I in an Adult Bovine Aortic Endothelial (ABAE) cell line and in Human Tumor cells lines is evaluated in three similar assays that measure growth inhibition. The assays are identified as follows:

PROTOCOL 1

PROTOCOL 2 and

PROTOCOL 3.

PROTOCOLS 1, 2, and 3 are described in greater detail hereinbelow. In general, according to PROTOCOLS 1 and 2, the target ABAE and/or Human Tumor cells are exposed to the compound of Formula I for 48 hours. PROTOCOL 3 exposes ABAE cells to the compounds for 4 days. A detailed description of the protocol is as follows:

Biological Protocols

PROTOCOL 1

Antiproliferative Activity in Human Tumor and Adult Bovine Aortic Endothelial Cell Lines (ABAE)

The antiproliferative activity of the compounds of Formula I of the present invention is evaluated in a panel comprised of human tumor cell lines and an adult bovine aortic endothelial cell line (ABAE). The human tumor cell lines are from 1) Ovarian tumors:

HTB161, A2780S and A2789/DDP; and

2) Colon tumors:

MIP, CACO2, and SW620.

All cell lines are maintained in log phase in RPMI 1640 media, supplemented with 5% fetal calf serum, penicillin/streptomycin and 2 mM L-glutamine. Cultures are renewed after 20 passages with cells from a fresh stock of batch-frozen early passage cells. Cell lines are routinely checked for mycoplasma contamination (Genprobe). In a laminar flow hood, cells ($1-5 \times 10^4$) are plated into 96-well microtiter plates in a volume of 0.1 ml/well with a bulk microtiter dispenser (Denley). Twenty-four hours after cell plating, test compounds are added in duplicate over a 5-log concentration range, starting with 100 microgram/ml, in a diluent such that the final concentration of dimethylsulfoxide in cell culture medium does not exceed 1% (v/v). At this concentration, dimethylsulfoxide has no effect on cell growth. Compounds are added using a Tomtec dispenser which simultaneously dispenses from one 96-well plate, containing the drug dilutions, to the plates containing the cells. After two days of continuous drug exposure, 50% cold trichloroacetic acid (TCA) is added to 10% final concentration to fix the cells, and after 60 minutes at 4° C., the TCA is aspirated and the plates are washed 5 times with deionized water using a microtiter plate washer. The number of cells on the plate are quantitated using a protein dye-binding assay (Monks et al., 1991). A 0.4% solution of the dye, sulforhodamine B, in glacial acetic acid is added to the plates, and the plates are washed 5 times with 1% glacial acetic acid using the automatic plate washed. The bound stain is solubilized with 0.1 ml of 10 mM Tris base. The optical densities are read from an automatic spectrophotometric plate reader (Dynatech) directly to a main frame computer (VAX 8600).

Positive controls, that include standard chemotherapeutic drugs (i.e., adriamycin, cisplatin, etc.), are included in every experiment.

Background optical density measurements (complete media−cells, and complete media+drug−cells) are automatically subtracted from the appropriate control and test wells. Mean values and standard errors are determined from duplicate wells. A measure is also made of the optical density at time when the drugs are added. The number of cells after treatment (P), as % of control, is calculated for every concentration of drug, as follows:

$$P = \frac{(T - C_o)}{(C - C_o)} \times 100$$

wherein:

T is optical density measurement for treated cells after 48 hours;

C is optical density measurement for untreated cells after 48 hours;

$C_o$ is optical density measurement for cells at the time of drug addition.

$IC_{50}$ of growth inhibition is calculated from the sets of P values using the RS-1 data package (BBN Software).

PROTOCOL 2

Antiproliferative Activity in Human Tumor Cell Lines

The antiproliferative activity of the compounds of Formula I is evaluated in the panel comprised of human tumor cell lines as listed in PROTOCOL 1. This assay is a slight modification of PROTOCOL 1. The modifications include:

1) each concentration for each compound is tested in a single well;

2) compounds are tested at 20, 4, 0.8, 0.16 microgram/ml and additionally in some experiments at 100 and 0.32 microgram/ml;

3) samples are pipetted into a 96-well plate for each of the cell lines by a Beckman Biomek 1000 SL robot;

4) after fixing with TCA each well is washed with 0.35 ml distilled water twice, not five times;

5) after staining with sulforhodamine B each well is washed 3 times, not five times;

6) the growth inhibition (I) as % of control, is calculated using the RS-1 data package (BBN Software), for every concentration of drug, as follows:

$$I = \frac{[1 - (T)]}{(C)} \times 100$$

wherein:

T is optical density measurement for treated cells after 48 hours;

C is optical density measurement for untreated cells after 48 hours;

7) $IC_{50}$ of growth inhibition is determined graphically from dose response curves, as is known in the art.

PROTOCOL 3

Antiproliferative Activity in Adult Bovine Aortic Endothelial (ABAE) Cell Line

ABAE cells are grown in DMEM media (Mediatech Washington, D.C.) supplemented with 10% calf serum (Hyclone). ABAE cells are plated in 24-well dishes at 8,000 cells/well, followed by the addition of increasing concentrations of 7-[substituted amino]-9-[(substituted glycyl) amido]-6-demethyl-6-deoxytetra-cyclines. After four days, the cells are detached and counted. In the control wells, cells did not reach confluency during experimental time. The growth inhibition (I) as % of control is calculated as follows:

$$I = \frac{[1 - (N_t - N_o)]}{(N_c - N_o)} \times 100$$

wherein:

$N_c$ is the number of cells in untreated wells;

$N_t$ is the number of cells in treated wells;

$N_o$ is the number of plated cells.

$IC_{50}$ of growth inhibition is determined from the sets of I values plotted by Kaleidograph software (Abelbeck Software).

Table 2 presents the results depicting the antiproliferative activity of the compounds of Formula I against an adult bovine aortic endothelial cell line (ABAE), as evaluated by PROTOCOL 1 and PROTOCOL 3. The results are presented in terms of $IC_{50}$ and are as follows.

TABLE 2

Antiproliferative Activity in Adult Bovine Aortic Endothelial (ABAE) Cell Line

| COMPOUND OF EXAMPLE NO. | $IC_{50}$ PROTOCOL 1 | PROTOCOL 3 |
|---|---|---|
| 4 | 2.4 | ND |
| 5 | 2.2 | ND |
| 2 | 6.6 | 3.0 |
| Prior Art Compound Minocycline | 6.8 | $\geq 50$ |

ND = Not Determined

In addition, FIG. 1 presents the dose response curve for the compound of Example 2 for the above ABAE cell line obtained by using PROTOCOL 3.

As can be seen from Table 2, the compounds of Formula I exhibit increased activity in inhibiting the proliferation of ABAE cells, as compared to the prior art compound Minocycline. Also as can be seen from FIG. 1, the difference between the prior art compound Minocycline and the compound of Example 2 is more significant in a 4 day assay (Protocol 3). It appears, that the prior art compound Minocycline is losing its activity upon incubation with cells, while the compound of Example 2 retains its activity. Minocycline inhibits 50% of cell growth at approximately 50 μg/ml, while the compound of Example 2 inhibits 50% of cell growth at approximately 3 μg/ml.

Table 3 presents the results depicting the antiproliferative activity of the compounds according to Formula I against a panel of Human Tumor Cell lines as evaluated by PROTOCOL 1 and PROTOCOL 2. The results are presented in terms of $IC_{50}$ values against each cell line and average $IC_{50}$ and are as follows.

Minocycline. Also, as can be seen from FIG. 2, even at the highest concentrations of compound of Example 8, there is no 100% inhibition of cell growth. This result means that even at the highest concentration of compound of Example 8 the cells continue to grow. Dead floating cells were not observed even at the highest concentration of compound of Example 8 or other compounds of Formula I. Taken together, these data indicate that the compounds of Formula I are inhibitors of cell growth, or cytostatic compounds, rather than cytotoxic compounds to the cells.

The data from both Tables 2 and 3 demonstrate that the compounds of Formula I are more potent in inhibiting endothelial and tumor cells, than the Minocycline compound utilized by Brem et al and Teicher et al. This is of particular importance as a more potent compound can inhibit tumor cells, endothelial cells, and vascular growth more effectively, thus permitting the use of smaller doses. Also, such compounds will have a greater efficacy for keeping tumor growth in check after chemotherapy or radiation therapy. This translates directly into a real benefit of requiring fewer repetitions of chemotherapy and radiation therapy to eradicate a tumor. Also, such compounds permit intervals between radiation or chemotherapy to be longer without significant tumor regrowth.

We claim:

1. A method for inhibiting angiogenesis and endothelial cell proliferation which comprises administering an effective inhibitory amount of a compound of formula I:

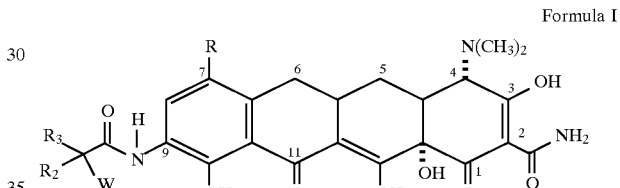

Formula I wherein

R is a (disubstituted) amino of the formula —N($R_4$)($R_5$) and ($R_4$) and ($R_5$) may be the same or different and are selected from straight or branched ($C_1$–$C_4$)alkyl, or [($C_3$–$C_6$)cycloalkyl]($C_1$–$C_4$)alkyl;

TABLE 3

Antiproliferative Activity in Human Tumor Cell Lines

| | OVARIAN TUMOR CELL LINES | | COLON TUMOR CELL LINES | | | | |
|---|---|---|---|---|---|---|---|
| COMPOUND FROM EXAMPLE NO. | A2780S $IC_{50}$ μg/ml | A2780/DDP $IC_{50}$ μg/ml | MIP $IC_{50}$ μg/ml | CACO2 $IC_{50}$ μg/ml | HTB 161 $IC_{50}$ μg/ml | SW620 $IC_{50}$ μg/ml | AVERAGE $IC_{50}$ FOR TUMOR CELL LINES |
| 4 | 2.3 | 2.3 | 2.8 | 1.9 | 2.0 | 2.7 | 2.3 |
| 3 | 2.4 | 2.7 | 2.45 | ND | 2.3 | 2.3 | 2.4 |
| 5 | 2.5 | 2.5 | 3.2 | 3.7 | 2.3 | 2.4 | 2.4 |
| 8 | 2.5 | 1.5 | 10.0 | 6.0 | 2.5 | 1.5 | 4.0 |
| 6 | 3.5 | 3.0 | 10.0 | 8.0 | 3.0 | 3.0 | 5.1 |
| 7 | 3.0 | 3.0 | 8.0 | 10.0 | 3.0 | 3.5 | 5.1 |
| 2 | 6.5 | 7.0 | 4.6 | 5.1 | 6.0 | 5.6 | 5.8 |
| Prior Art Compound Minocycline | 6.1 | 6.1 | 6.1 | 9.0 | 5.8 | 6.5 | 6.6 |

ND = Not Determined

FIG. 2 shows graphically the dose response curve for the compound of Example 8 against the 6 tested Human Tumor Cell lines.

As can be seen from Table 3, the compounds of Formula I exhibit increased activity in inhibiting the proliferation of tumor cell lines as compared to the prior art compound W is ($R_1$)$_2$—N—; $R_1$—NH— or ($C_2$–$C_5$)azacycloalkane wherein $R_1$ is a straight chain ($C_1$–$C_7$)alkyl;
$R_2$ is hydrogen or ($C_1$–$C_3$)alkyl;
$R_3$ is hydrogen or ($C_1$–$C_3$)alkyl; or a pharmaceutically acceptable salt thereof;

alone or in combination with a therapeutic agent used in the treatment of an angiogenic disorder;

to a warm blooded animal having a disorder characterized by the undesired proliferation of endothelial cells.

2. The method according to claim 1, wherein the compound of formula I is selected from

[4S-(4α, 12aα-]-4,7-bis(dimethylamino)-9-[[(dimethylamino)acetyl]amino]]-1,4,4a,5,5a,6,11,12a-octahydro-3,10,12,12a-tetrahydroxy-1,11-dioxo-2-naphthacenecarboxamide dihydrochloride;

[7S-(7α, 10aα)]-N-[9-(aminocarbonyl)-4,7-bis(dimethylamino)-5,5a,6,6a,7,10,10a,12-octahydro-1,8,10a,11-tetrahydroxy-10,12-dioxo-2-naphthacenyl]-1-pyrrolidine-acetamide dihydrochloride;

[4S-(4α, 12aα)]-4,7-bis(dimethylamino)-9-[(hexylamino)-acetyl]amino]-1,4,4a,5,5a,6,11,12a-octahydro-3,10,12,12a-tetrahydroxy-1,11-dioxo-2-naphthacenecarboxamide dihydrochloride;

[4S-(4α, 12aα)]-4,7-bis(dimethylamino)-9-[[(heptylamino)-acetyl]amino ]-1,4,4a,5,5a,6,11,12a-octahydro-3,10,12,12a-tetrahydroxy-1,11-dioxo-2-naphthacenecarboxamide dihydrochloride;

[4S-(4α, 12aα)]-4-(dimethylamino)-9-[[(dimethylamino)-acetyl]amino ]-7-(dipropylamino)-1,4,4a,5,5a,6,11,12a-octahydro-3,10,12,12a-tetrahydroxy-1,11-dioxo-2-naphthacenecarboxamide sulfate (1:1);

7-[butyl(cyclopropylmethyl)amino]-4-(dimethylamino)-9-[[(dimethylamino)acetyl]amino ]-1,4,4a,5,5a,6,-11,12a-octahydro-3,10,12,12a-tetrahydroxy-1,11-dioxo-2-naphthacenecarboxamide sulfate (1:2); and

[4S-(4α, 12aα)]-7-[bis(2-methylpropyl)amino]-4-(dimethylamino)9-[[(dimethylamino)acetyl]amino]-1,4,4a,5,5a,6,11,12a-octahydro-3,10,12,12a-tetrahydroxy-1,11-dioxo-2-naphthacenecarboxamide sulfate.

3. The method according to claim 2 wherein the compound of formula I is selected from [4S-(4α, 12aα-]-4,7-bis(dimethylamino)-9-[[(dimethylamino)acetyl]amino]]-1,4,4a,5,5a,6,11,12a-octahydro-3,10,12,12a-tetrahydroxy-1,11-dioxo-2-naphthacenecarboxamide dihydrochloride;

[7S-(7α, 10aα)]-N-[9-(aminocarbonyl)-4,7-bis(dimethylamino)-5,5a,6,6a,7,10,10a,12-octahydro-1,8,10a,11-tetrahydroxy-10,12-dioxo-2-naphthacenyl]-1-pyrrolidine-acetamide dihydrochloride;

[4S-(4α, 12aα)]-4,7-bis(dimethylamino)-9-[(hexylamino)-acetyl]amino ]-1,4,4a,5,5a,6,11,12a-octahydro-3,10,12,12a-tetra-hydroxy-1,11-dioxo-2-naphthacenecarboxamide dihydrochloride; and

[4S-(4α, 12aα)]-7-[bis(2-methylpropyl)amino]-4-(dimethylamino)9-[[(dimethylamino)acetyl]amino]-1,4,4a,5,5a,6,11,12a-octahydro-3,10,12,12a-tetrahydroxy-1,11-dioxo-2-naphthacenecarboxamide sulfate.

4. The method of claim 1, wherein the effective amount of the compound of Formula I is from about 0.10 mg to 30.0 mg per kg of body weight.

5. The method of claim 4, wherein the amount is from about 1.0 mg and 10.0 mg per kg of body weight.

6. The method of claim 1, wherein the compound of formula I is embedded in a biocompatible controlled release matrix delivery device.

7. A composition for inhibiting angiogenesis and endothelial cell proliferation which composition comprises an amount effective for inhibiting endothelial cell proliferation of a compound of formula I:

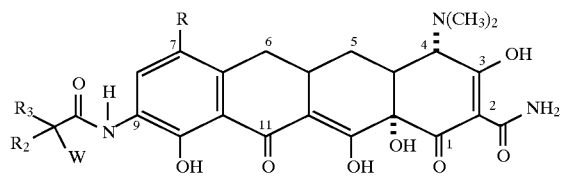

Formula I wherein

R is a disubstituted amino of the formula —N(R$_4$)(R$_5$) and (R$_4$)and (R$_5$) may be the same or different and are selected from straight or branched (C$_1$–C$_4$)alkyl, or [(C$_3$–C$_6$)cycloalkyl](C$_1$–C$_4$)alkyl;

W is (R$_1$)$_2$—N—; R$_1$—NH— or (C$_2$—C$_5$)azacycloalkane wherein

R$_1$ is a straight chain (C$_1$–C$_7$)alkyl;

R$_2$ is hydrogen or (C$_1$–C$_3$)alkyl;

R$_3$ is hydrogen or (C$_1$–C$_3$)alkyl; or a pharmaceutically acceptable salt thereof;

in a pharmaceutical carrier for administration to a warm blooded animal having a disorder characterized by the uncontrolled proliferation of endothelial cells.

8. The composition of claim 7 further comprising a therapeutic agent used in the treatment of an angiogenic disorder.

9. The composition of claim 8 wherein said therapeutic agent comprises inethotrexate, angiostatin, genistein, suramin, pentosan polysulfate, thalidomide and 2-methoxyestradiol.

10. The composition of claim 7 further comprising a chemotherapeutic agent.

11. The composition of claim 10 wherein said chemotherapeutic agent comprises an anti-cancer agent selected from mephalan, cyclophosphamide, methotrexate, adriamycin and bleomycin.

12. The composition according to claim 7 wherein the compound of formula I is selected from

[4S-(4α, 12aα-]-4,7-bis(dimethylamino)-9-[[(dimethylamino)acetyl]amino]]-1,4,4a,5,5a,6,11,12a-octahydro-3,10,12,12a-tetrahydroxy-1,11-dioxo-2-naphthacenecarboxamide dihydrochloride;

[7S-(7α, 10aα)-N-[9-(aminocarbonyl)-4,7-bis(dimethylamino)-5,5a,6,6a,7,10,10a,12-octahydro-1,8-10a,11-tetrahydroxy-10,12-dioxo-2-naphthacenyl]-1-pyrrolidine-acetamide dihydrochloride;

[4S-(4α, 12aα)]-4,7-bis(dimethylamino)-9-[(hexylamino)-acetyl]amino]-1,4,4a,5,5a,6,-11,12a-octahydro-3,10,12,12a-tetrahydroxy-1,11-dioxo-2-naphthacenecarboxamide dihydrochloride;

[4S-(4α, 12aα)]-4,7-bis(dimethylamino)-9-[[(heptylamino)acetyl]amino]-1,4,4a,5,5a,6,11,12a-octahydro-3,10,12,12a-tetrahydroxy-1,11-dioxo-2-naphthacenecarboxamide dihydrochloride;

[4S-(4α, 12aα)]-4-(dimethylamino)-9-[[(dimethylamino) acetyl]amino]-7-(dipropylamino)-1,4,4a,5,5a,6,11,12a-octahydro-3,10,12,12a-tetrahydroxy-1,11-dioxo-2-naphthacenecarboxamide sulfate (1:1);

7-[butyl(cyclopropylmethyl)amino]-4-(dimethylamino)-9-[[(dimethylamino)acetyl]amino]-1,4,4a,5,5a,6,11,12a-octahydro-3,10,12,12a-tetrahydroxy-1,11-dioxo-2-naphthacenecarboxamide sulfate (1:2); and

[4S-(4α, 12aα)]-7-[bis(2-methylpropyl)amino]-4-(dimethylamino)9-[[(dimethylamino)acetyl]amino]-1,4,4a,5,5a,6,11,12a-octahydro-3,10,12,12a-tetrahydroxy-1,11-dioxo-2-naphthacenecarboxamide sulfate.

13. The composition according to claim 12 wherein the compound of formula I is selected from [4S-(4α, 12aα-]-4,7-bis(dimethylamino)-9-[[(dimethylamino)acetyl]amino]]-1,4,4a,5,5a,6,11,12a-octahydro-3,10,12,12a-tetrahydroxy-1,11-dioxo-2-naphthacenecarboxamide dihydrochloride;

[7S-(7α, 10aα)]-N-[9-(aminocarbonyl)-4,7-bis(dimethylamino)-5,5a,6,6a,7,10,10a,12-octahydro-1,8-10a,11-tetrahydroxy-10,12-dioxo-2-naphthacenyl]-1-pyrrolidine-acetamide dihydrochloride;

[4S-(4α, 12aα)]-4,7-bis(dimethylamino)-9-[(hexylamino)-acetyl]amino]-1,4,4a,5,5a,6,-11,12a-octahydro-3,10,12,12a-tetrahydroxy-1,11-dioxo-2-naphthacenecarboxamide dihydrochloride; and

[4S-(4α, 12aα)]-7-[bis(2-methylpropyl)amino]-4-(dimethylamino)9-[[(dimethylamino)acetyl]amino]-1,4,4a, 5,5a, 6,11,12a-octahydro-3,10,12,12a-tetrahydroxy-1,11-dioxo-2-naphthacenecarboxamide sulfate.

14. The composition of claim 7, wherein the effective amount of the compound of Formula I is from about 0.10 mg to 30.0 mg per kg of body weight.

15. The composition of claim 14, wherein the amount is from about 1.0 mg and 10.0 mg per kg of body weight.

16. The composition of claim 7, wherein the compound of formula I is embedded in a biocompatible controlled release matrix delivery device.

* * * * *